(12) United States Patent
Dalton et al.

(10) Patent No.: US 12,107,400 B1
(45) Date of Patent: Oct. 1, 2024

(54) ADJUSTABLE ORGANIZER

(71) Applicants: William Dalton, Kansas City, MO (US); Lisa Sprague, St. Joseph, MO (US)

(72) Inventors: William Dalton, Kansas City, MO (US); Lisa Sprague, St. Joseph, MO (US)

(*) Notice: Subject to any disclaimer, the term of this patent is extended or adjusted under 35 U.S.C. 154(b) by 0 days.

(21) Appl. No.: 18/101,206

(22) Filed: Jan. 25, 2023

(51) Int. Cl.
| | |
|---|---|
| *H02G 3/32* | (2006.01) |
| *A61B 5/321* | (2021.01) |
| *H02G 3/00* | (2006.01) |
| *H02G 3/02* | (2006.01) |
| *H02G 3/04* | (2006.01) |

(52) U.S. Cl.
CPC .............. *H02G 3/02* (2013.01); *A61B 5/321* (2021.01); *H02G 3/0437* (2013.01)

(58) Field of Classification Search
CPC .......... H02G 3/02; H02G 3/0437; H02G 3/00; H02G 3/32; A61B 5/321
See application file for complete search history.

(56) References Cited

U.S. PATENT DOCUMENTS

| | | | |
|---|---|---|---|
| 6,620,105 B2 | 9/2003 | Sharpe | |
| 7,712,709 B2* | 5/2010 | Winchester | F16L 3/223 |
| | | | 248/89 |
| 2009/0302148 A1* | 12/2009 | Auclair | B65D 85/04 |
| | | | 242/588.2 |
| 2010/0163278 A1* | 7/2010 | Grelck | H05K 7/1491 |
| | | | 174/135 |
| 2015/0089774 A1* | 4/2015 | Kalejaiye | H02G 3/32 |
| | | | 24/122.3 |
| 2023/0322104 A1* | 10/2023 | Michael | B60L 53/18 |
| | | | 320/109 |

FOREIGN PATENT DOCUMENTS

WO WO-2019092457 A1 * 5/2019 ........ A61M 16/0497

* cited by examiner

*Primary Examiner* — Tan Le
(74) *Attorney, Agent, or Firm* — BRADLEY IP, LLC; Sean T. Bradley

(57) ABSTRACT

The present invention provides an adjustable organizer for cords or electrical leads. Advantageously, the position of the organizer can be adjusted without having to disassemble the organizer from the cords or electrical leads and with only one hand. The organizer can remain attached to the cords or electrical leads for the lifetime of the cords or electrical leads. The organizer can be cleaned or sterilized using the techniques that are suitable for cleaning or sterilizing the attached cords or electrical leads.

14 Claims, 2 Drawing Sheets

ADJUSTABLE ORGANIZER

FIELD OF THE INVENTION

The present invention relates to adjustable devices to organize and change the positions of cords or electrical leads especially for cords or electrical leads that are attached to medical devices.

BACKGROUND OF THE INVENTION

Electrocardiograms (ECGs or EKGs), electroencepalograms (EEGs), electromyograms (EMGs), and electrooculograms (EOGs) are machines that measure various electrical biopotentials of a human body. To do so, each machine uses from one to a dozen electrical leads that are attached to various parts of a patient's body to measure electrical activity. Similarly, eye movement is measured by electrodes placed above, below, and at the side of each eye using different equipment.

There are many different types of each of these machines, but they all have the same basic features. The machines have a control panel where the operator can input the patient's information, a paper roll that records the tracing of the heart's electrical activity, and from one to a dozen leads that attach to various parts of a patient's body.

Multi-lead machines provide more detailed data of a patient's electrical activity. These machines are used in hospitals, doctor's offices, and other clinical settings and are regularly moved from one position to another and one room to another. Because the electrical leads for these machines need to be attached to various parts of a patient's body and the environments where the readings are taken vary, these electrical leads are relatively long. In addition, besides measuring electrical signals, many medical devices require additional connections such as fluid lines or fiber-optic connections. These leads and any other wires or lines are regularly moved about during use or transport and should be checked for signs of wear, damage, or entanglements as any of these can be detrimental to the performance of a machine and care of a patient.

Since these machines are used in hospitals and other clinical settings, they should be designed to be easily manipulated using surgical gloves. Push-pull designs for engagement are preferred for electrical leads. Connectors and cords can be color or mechanically-coded to ensure that they are plugged into the proper receptacles. In many cases, the patient connector is attached to a probe or similar device intended for one-time use, but the mating connector and associated electrical lead or wire on the instrument itself should be robust enough to withstand as many as 10,000 mating cycles. The lifetimes of electrical leads can be shortened due to entanglements that occur during moving machines from one location to another or when attaching and then disconnecting cords or leads from a patient.

SUMMARY OF THE INVENTION

The present invention provides an adjustable organizer for cords or electrical leads. Advantageously, the position of the organizer can be adjusted without having to separate the organizer from the cords or electrical leads. The invention can remain attached to the cords or electrical leads for the lifetimes of the cords or electrical leads. The organizer can be cleaned or sterilized using the techniques that are suitable for cleaning or sterilizing the attached cords or electrical leads.

The invention is particularly suitable for use in hospitals or other clinical settings because the position of the organizer can be adjusted by a user with only one hand. Those of skill in the art will appreciate that any task that can be accomplished with one hand in a setting that requires sterile techniques reduces physical waste and the amount of time to complete the task because the user does not need to repeatedly remove and replace potentially contaminated gloves.

Advantageously the position of an organizer of the invention can be repeatedly adjusted to accommodate patients of different sizes and for use on a variety of machines, particularly medical machines, that use multiple cords or electrical leads and are repeatedly moved to different areas or positions. Skilled artisans will appreciate that organizers of the invention can be used to organize and prevent the entanglement of cords or electrical leads that can occur during such repeated movements. Preventing such entanglements reduces the amount of time required for an operator to set up or disconnect a machine, and reduces the chance of the cords or electrical leads being damaged and the usable lifetimes of the cords or electrical leads being shortened.

The present invention provides an organizer that comprises a housing and a closure key. The housing has a top, a bottom, two long sides and two short sides. Each long side of the housing has two or more lateral openings, preferably keyhole openings, that extend from a first long side to a second long side of the housing. A preferred keyhole opening has an upper rounded end and a vertical shaft that extends through the bottom of the housing.

At least one short side, i.e. a first short side, of the housing has a longitudinal opening that extends through the housing and through the vertical shafts of the two or more lateral openings. The closure key comprises a tongue and a stop.

The organizer is flexible. Those of skill in the art will be aware that a variety of plastics are suitable for use in a clinical setting and can be used to make the invention. For example, an organizer of the invention may comprise a thermoplastic material. Preferred thermoplastic materials include polypropylenes, polycarbonates, polyethylenes, or combinations thereof that can be cleaned while an organizer is attached to one or more cords or electrical leads.

In preferred embodiments of the invention, the opening in the first short side extends through a second short side of the housing to the exterior of the housing. An advantage of having the opening extend through both short sides of embodiments of the invention is that the closure key can be inserted into the housing from either short side of the housing, which allows both right and left-handed users equal access to assembling an organizer of the invention.

Herein, for ease of discussion and clarity, the lateral openings in housing may be referred to as keyhole openings. In a preferred embodiment of the invention the lateral opening has a keyhole shape. But skilled artisans will appreciate the lateral openings do not necessarily require a keyhole shape. For example, lateral openings may be shaped to include corners.

Those of skill in the art will appreciate that while the keyhole shape is preferred for lateral openings in the longitudinal sides of the housing, the lateral openings may have a variety of shapes and sizes. It is only necessary that any specific opening is of sufficient size to accommodate a cord or electrical lead and when the organizer is not flexed that a cord or electrical lead remains in its position relative to the organizer, and the organizer does not freely slide along the cord or electrical lead.

In preferred embodiments, the diameter of each upper rounded end of a keyhole opening is larger than the diameter of a cord or electrical lead, and the lateral width of each vertical shaft of a keyhole opening is less than the diameter of each upper rounded end of the keyhole openings and equal to or greater than the diameter of the cord or electrical lead.

The invention also provides a method of using an organizer comprising inserting a first cord or electrical lead into a housing that comprises a top, a bottom, two long sides and two short sides. Each long side has two or more keyhole openings that extend laterally from a first long side to a second long side, and each keyhole opening has an upper rounded end and a vertical shaft that extends through the bottom of the housing. In the housing, at least a first short side has an opening that extends longitudinally through the length of the housing and the vertical shafts of the two or more keyhole openings. A first cord or electrical lead is inserted through a first vertical shaft and into a first upper rounded end. A second cord or electrical lead is inserted through a second vertical shaft and into a second upper rounded end. A tongue of a closure key, wherein the closure key comprises a tongue and a stop, is inserted through the opening in the first short side and the vertical shafts of the two or more keyhole openings and the housing until the stop on the closure key contacts the first short side. A user compresses the assembled organizer so that the assembled organizer slides along the lengths of the cords or electrical leads to a first position. The user can then compress the assembled organizer so that the assembled organizer slides along the lengths of the cords or electrical leads to a desired second position.

The first position can be a position that is suitable for using a machine that is attached to the cords or electrical leads, and the second position can be a position that is a storage position. Alternatively, the first position can be a storage position and the second position can be a position suitable for using a machine that is attached to the cords or electrical leads. Those of skill in the art will appreciate that there may be other purposes associated with other positions to which a user may desire to move an assembled organizer.

Those of skill in the art will appreciate that methods of using an organizer of the invention can further comprise inserting at least one additional second cord or electrical lead through at least one additional second vertical shaft and into at least one additional second upper end of an organizer.

Methods of using an organizer of the invention further comprise compressing an assembled organizer repeatedly so that the assembled organizer slides repeatedly along the cords or electrical leads to a desired first, second, or third position.

The invention also provides a method of making an organizer comprising a flexible housing and a flexible closure key. The housing comprises a top, a bottom, two long sides and two short sides. Each long side of an organizer has two or more lateral openings, preferably keyhole openings, that extend from a first long side to a second long side. At least a first short side of the housing has a longitudinal opening that extends through the length of the housing and the vertical sections (shafts) of the two or more lateral openings. The closure key comprises a tongue and a stop. An assembled organizer is formed by inserting the tongue of the closure key into the housing through the longitudinal opening in the first short side until the stop of the closure key is in contact with the first short side of the housing.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Further, while specific advantages of the invention are detailed herein, various embodiments may include some, none, or all of these enumerated advantages.

BRIEF DESCRIPTION OF DRAWINGS

The following drawings form part of the present specification and are included to further demonstrate certain aspects of the invention. The invention may be better understood by reference to one or more of these drawings in combination with the detailed description presented herein. Unless specifically noted, articles depicted in the drawings are not necessarily drawn to scale.

DETAILED DESCRIPTION

The invention provides compositions and methods that reduce the time and effort that is required to set up or disconnect a medical machine from a patient. Advantageously, the invention also provides a means of keeping cords or electrical leads that are attached to a device organized and less likely to become entangled or damaged.

Once installed, this device holds 1 to 12 or more cords, lines, wires, or electrical leads in place when a machine, such as an ECG monitor, is not in use, preventing them from becoming tangled. When ready for use, the user manually compresses the device so that it slides along the attached cords, lines, wires, or electrical leads so that they can be attached to appropriate electrode tabs and a patient. After completing use of the device, the user removes the attached leads and compresses the device so that it slides along the leads to a desired position, e.g. a storage position, while keeping the leads organized and preventing entanglement before the next use. Advantageously, the user can compress the device by using only one hand.

Devices of the invention are durable, preferably latex free, and made of plastic. Preferably, the plastic is a thermoplastic elastomer or a combination of thermoplastic elastomers (aka TPUs) so that the device fits easily over the cords, lines, wires, or electrical leads that are in common use in hospitals and other clinical settings. Advantageously, devices of the invention are maintenance free and if operated as intended are expected to last for at least the usable lifetimes of the attached cords, lines, wires, or electrical leads.

Figure 1:
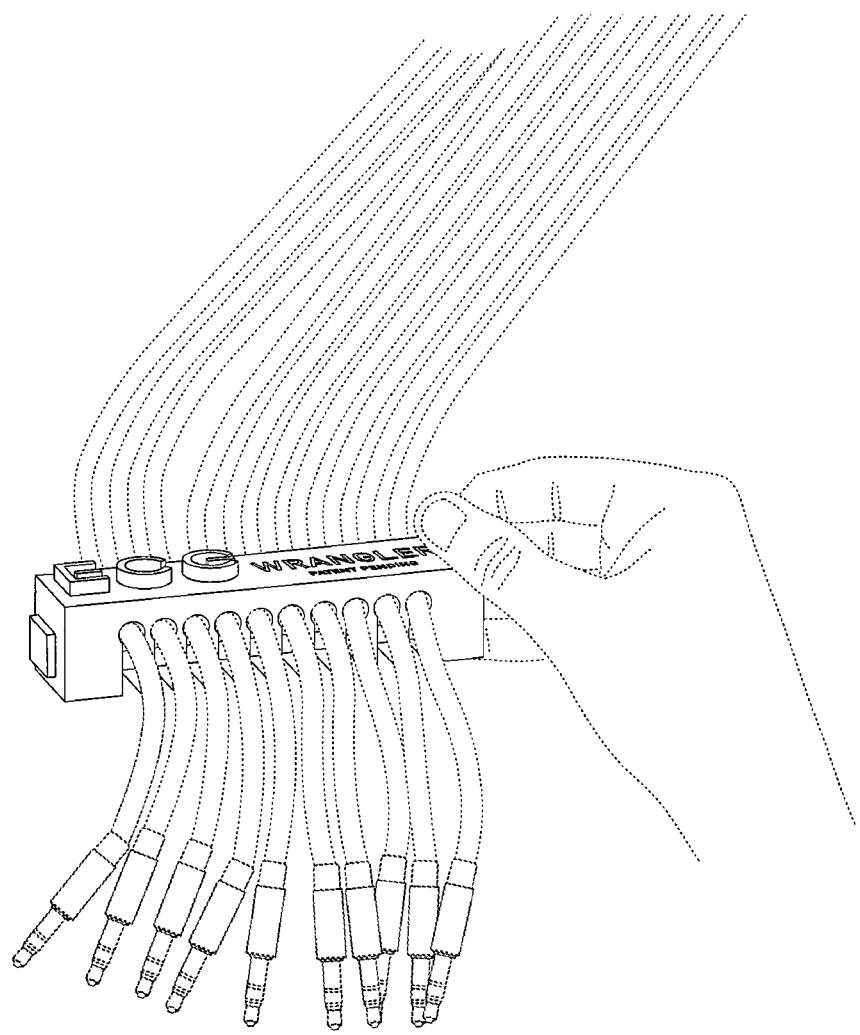
FIG. 1 illustrates an embodiment of the invention in context. All objects and features shown in broken lines are for illustrative purposes only and form no part of the claimed invention.
Figure 2:
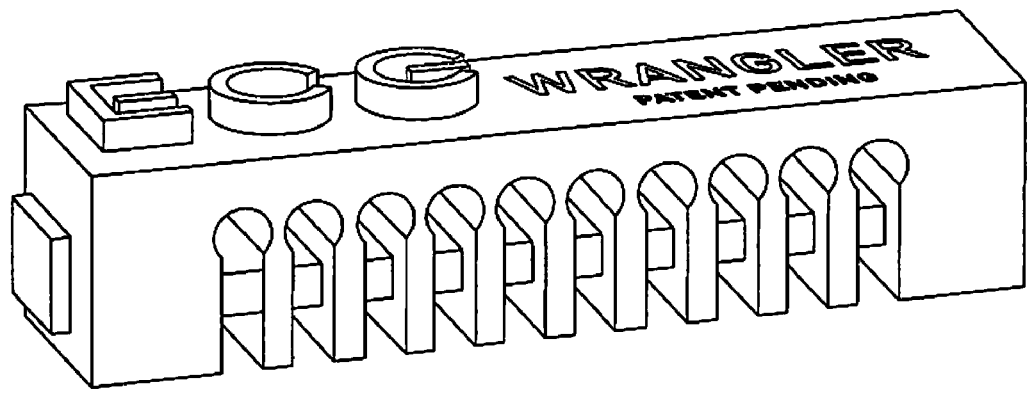
FIG. 2 is a front perspective view of an assembled preferred embodiment of the invention.
Figure 3:
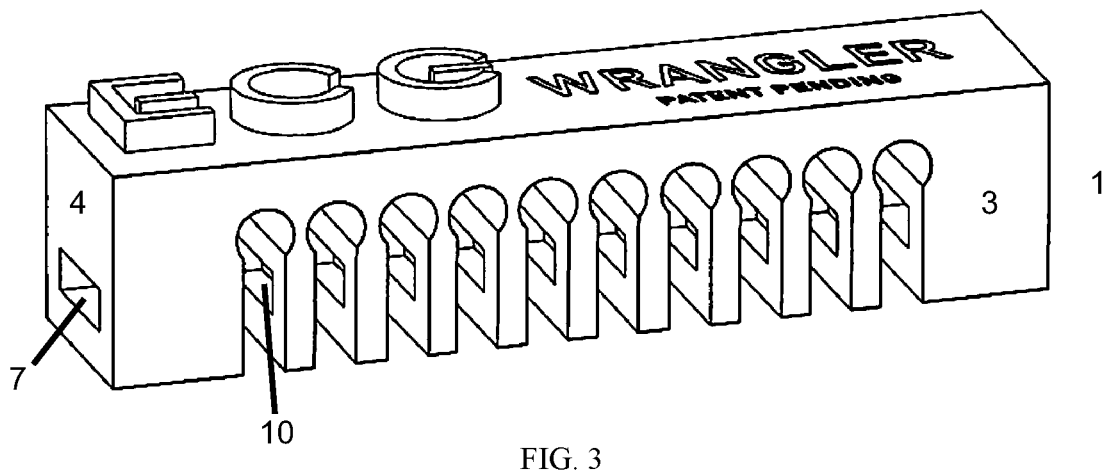
FIG. 3 is a front perspective view of the housing.
Figure 4:
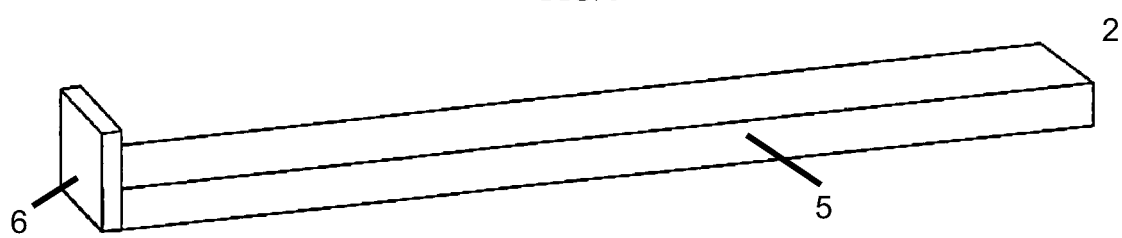
FIG. 4 is a front perspective view of a closure key.
Figure 5:
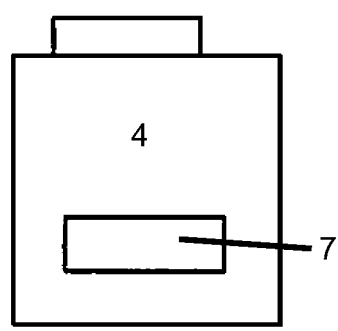
FIG. 5 is a side view of the short side of the body section that illustrates the location of the opening for the closure key.

An exemplary embodiment of the invention is illustrated in FIGS. 1-6. FIGS. 1 and 2 illustrate the embodiment in context (FIG. 1) and when fully assembled (FIG. 2). A device of the invention has two principal components: a housing 1 and a closure key 2. While it is preferred that each principal component comprises a single piece, those of skill in the art will appreciate that each component may comprise multiple separate pieces that when joined together function as described herein.

The housing 1 has a top, a bottom, two long sides, and two short sides. See FIG. 3. Each long side 3 has more than one lateral opening 10 that extends from one long side 3 to the other long side 3. At least one short side 4 has a longitudinal opening 7 that extends through the short side 4, the lateral openings 10, and into the second short side 4. In preferred embodiments of the invention, the longitudinal opening 7 extends completely through the second short side 4 to the exterior of the housing 1. The longitudinal opening 7 is located in the short side 4 so that when the closure key 2 is inserted into the opening 7 the closure key 2 does not interfere with any of the cords, lines, wires, or electrical leads that are attached to the device. See FIG. 5.

Figure 6:
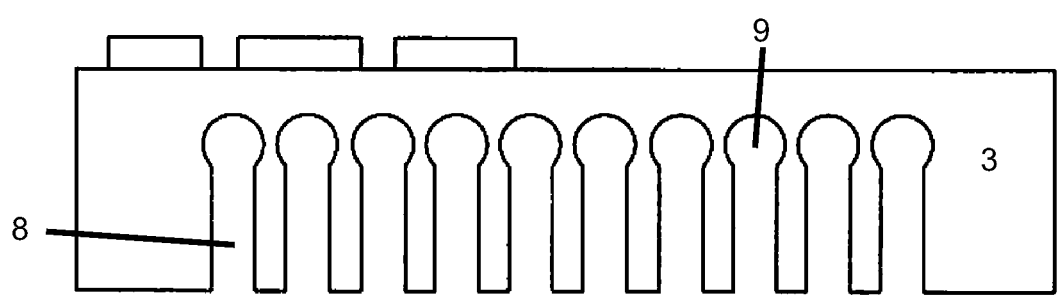
FIG. 6 is a side view of the long side of the body section.

A preferred exemplary shape for the lateral opening 10 is illustrated in FIG. 6. The lateral opening 10 has two functional parts: a vertical shaft 8 and an upper end 9. Each upper end 9 has a diameter (longitudinal diameter or width) that is equal to or greater than the diameter of a cord, line, wire, or electrical lead that is intended to be inserted into the device. Each vertical shaft 8 has a width (longitudinal diameter) that is greater than or equal to the diameter of the cord, line, wire, or electrical lead that is intended to be inserted into the device and preferably is less than the diameter of the upper end 9. A preferred shape for a lateral opening 10 is a keyhole shape. Those of skill in the art will appreciate that other shapes may be used for a lateral opening, and the opening will function as intended.

The closure key 2 has a tongue 5 that extends longitudinally, and a stop 6 at a near end of the tongue 5. See FIG. 4. The tongue 5 is of sufficient length to extend through the lateral openings 10, preferably all of the openings, in the housing 1. Preferably, the tongue 5 is sufficiently long to extend at least partially into the second short side 4 of the housing 1. Alternatively, the tongue 5 may be of sufficient length to extend to the exterior of the second short side 4. When the tongue 5 is inserted into the housing 1 through the longitudinal opening 7, the stop 6 prevents the closure key 2 from being inserted any further into the housing 1. That is, when the stop 6 is in contact with the adjacent short side 4 the closure key 2 is fully inserted into the housing 1 and the device is assembled.

Those of skill in the arts will recognize that the stop and tongue can have a wide variety of shapes and achieve the desired result. Thus, while the stop and tongue are illustrated in the drawings as being polygonal in shape, they may be spherical, ovoid, tubular, polyhedron, or otherwise shaped, as long as the closure key functions as intended. Similarly, the housing and its various parts may have alternative shapes, as long as the housing and its various parts function as intended.

By way of example, for devices that can accommodate ten cords, lines, wires, or electrical leads the housing 1 has an overall length of 85 to 92 mm, an overall width of 15 to 24 mm, and an overall height of 15 to 24 mm. For devices able to accommodate ten cords, lines, or leads, the preferred housing dimensions are 88 to 89 mm in length, 19 to 20 mm in width, and 19 to 20 mm in height, and the preferred dimensions for a longitudinal opening are 11 to 12 mm by 3 to 4 mm by 88 to 89 mm.

Preferred suitable materials for the manufacture of devices of the invention include plastics that can be sterilized using an accepted sterilization method such as autoclaving, hot air sterilization, hydrogen peroxide plasma, radiation, or a microbiocidal gas such as formaldehyde or ethylene oxide. Those of skill in the art will recognize that devices of the inventions or portions of them may include alternative materials such as one or more metal components, as long as, the alternative materials do not impair the intended functions of the devices.

Unless defined otherwise, all technical and scientific terms used herein have the same meaning as is commonly understood by one of skill in the art to which this invention belongs at the time of filing. The terminology used herein is for the purpose of describing specific embodiments of the invention and is not intended to be limiting. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular unless the content clearly dictates otherwise. Herein, the use of "of" means "and/or" unless stated otherwise. Furthermore, the use of the term "including", as well as other forms such as "includes" and "included" is not limiting. As used herein, "each" refers to each member of a set or each member of a subset of a set.

What is claimed is:

1. An organizer having a housing and a closure key, wherein the organizer is flexible; the housing comprises a top, a bottom, two long sides and two short sides, wherein a first long side has two or more lateral openings that extend from the first long side to a second long side and through the bottom of the housing, and wherein at least a first short side has a longitudinal opening that extends the length of the housing and through the two or more lateral openings; and the closure key comprises a tongue and a stop, wherein the tongue of the closure key inserts into the housing through the longitudinal opening until the stop of the closure key contacts the first short side of the housing.

2. The organizer of claim 1, wherein the longitudinal opening extends through the second short side to the exterior of the housing.

3. The organizer of claim 1, wherein an upper end of each of the two or more lateral openings has a diameter that is larger than the diameter of a cord or electrical lead, and a vertical shaft of each of the two or more lateral openings has a width that is less than the diameter of the upper end of the two or more lateral openings and equal to or greater than the diameter of a cord or electrical lead.

4. The organizer of claim 1, wherein the two or more lateral openings are keyhole openings, wherein each keyhole opening has an upper rounded end and a vertical shaft that extends through the bottom of the housing.

5. The organizer of claim 4, wherein the upper rounded end of each keyhole opening has a diameter that is larger than the diameter of a cord or electrical lead, and the vertical shaft of each keyhole opening has a width that is less than the diameter of the upper end of the keyhole opening and equal to or greater than the diameter of a cord or electrical lead.

6. The organizer of claim 1, wherein the organizer comprises a thermoplastic material.

7. The organizer of claim 6, wherein the thermoplastic material comprises a polypropylene, polycarbonate, polyethylene, or a combination thereof.

8. A method of using an organizer comprising
   a. inserting a first cord or electrical lead into a housing that comprises a top, a bottom, two long sides and two short sides, wherein a first long side has two or more lateral openings that extend from the first long side to a second long side and through the bottom of the housing, and at least a first short side has a longitudinal opening that extends through the housing and the two or more lateral openings, wherein the first cord or electrical lead is inserted into a first lateral opening;
b. inserting a second cord or electrical lead into a second lateral opening;
c. inserting a tongue of a closure key, wherein the closure key comprises the tongue and a stop, through the longitudinal opening in the first short side and the two or more lateral openings of the housing until the stop contacts the first short side of the housing;
d. compressing an assembled organizer to allow the assembled organizer to slide along the cords or electrical leads to a first position;
e. releasing the compression on the assembled organizer;
f. compressing the assembled organizer to allow the assembled organizer to slide along the cords or electrical leads to a desired second position; and
g. releasing the compression on the assembled organizer.

9. The method of using an organizer of claim 8 further comprising inserting at least one additional second cord or electrical lead through at least one additional second lateral opening.

10. The method of using an organizer of claim 8 further comprising compressing the assembled organizer repeatedly to allow the assembled organizer to slide repeatedly along the cords or electrical leads to the desired first position or second position.

11. The method of using an organizer of claim 8, wherein the assembled organizer is compressed by a user by using only one hand.

12. A method of making an organizer comprising
a. making a housing that is flexible and comprises a top, a bottom, two long sides and two short sides, wherein each long side has two or more lateral openings that extend from a first long side to a second long side and each lateral opening has an upper closed end and a vertical shaft that extends through the bottom of the housing, and wherein at least a first short side has a longitudinal opening that extends through the housing and the vertical shafts of the two or more keyhole openings;
b. making a closure key that is flexible and comprises a tongue and a stop; and
c. inserting the closure key into the housing so that the tongue of the closure key inserts into the housing through the longitudinal opening until the stop of the closure key contacts the first short side of the housing to form an assembled organizer.

13. The method of claim 12, wherein the organizer comprises a thermoplastic material.

14. The method of claim 13, wherein the thermoplastic material comprises a polypropylene, polycarbonate, polyethylene, or a combination thereof.

* * * * *